United States Patent [19]
Mandeville, III et al.

[11] Patent Number: 6,034,129
[45] Date of Patent: Mar. 7, 2000

[54] IONIC POLYMERS AS ANTI-INFECTIVE AGENTS

[75] Inventors: W. Harry Mandeville, III, Lynnfield; Thomas X. Neenan, Boston; Stephen Randall Holmes-Farley, Arlington, all of Mass.

[73] Assignee: GelTex Pharmaceuticals, Inc., Waltham, Mass.

[21] Appl. No.: 08/670,764

[22] Filed: Jun. 24, 1996

[51] Int. Cl.$^7$ .......................... A61K 31/14; A61K 31/16; A61K 31/74

[52] U.S. Cl. .......................... 514/549; 514/627; 514/642; 514/643

[58] Field of Search .................................... 514/549, 627, 514/642, 643

[56] References Cited

U.S. PATENT DOCUMENTS

| | | | |
|---|---|---|---|
| 3,923,973 | 12/1975 | Green et al. | 424/78 |
| 3,929,990 | 12/1975 | Green et al. | 424/78 |
| 3,929,991 | 12/1975 | Steward et al. | 424/78.36 |
| 3,961,042 | 6/1976 | Green et al. | 424/78 |
| 4,005,193 | 1/1977 | Green et al. | 424/168 |
| 4,025,617 | 5/1977 | Green et al. | 424/78 |
| 4,026,945 | 5/1977 | Green et al. | 526/294 |
| 4,035,480 | 7/1977 | Green et al. | 424/78.32 |
| 4,113,709 | 9/1978 | Quinlan | 424/78 |
| 4,166,846 | 9/1979 | Shigematsu et al. | 424/81 |
| 4,206,295 | 6/1980 | Wagner et al. | 525/410 |
| 4,217,429 | 8/1980 | Wagner et al. | 525/411 |
| 4,379,137 | 4/1983 | Ehlers et al. | 424/78 |
| 4,407,791 | 10/1983 | Stark | 424/78.04 |
| 4,532,128 | 7/1985 | Sheldon et al. | 424/78 |
| 4,604,404 | 8/1986 | Munson, Jr. et al. | 514/494 |
| 4,621,120 | 11/1986 | Hollister | 525/327.1 |
| 4,826,924 | 5/1989 | Kourai et al. | 525/331.3 |
| 4,843,130 | 6/1989 | Kourai et al. | 525/331.3 |
| 4,960,590 | 10/1990 | Hollis et al. | 424/78 |
| 5,104,649 | 4/1992 | Jansson et al. | 424/78.31 |
| 5,142,010 | 8/1992 | Olstein | 526/248 |
| 5,149,524 | 9/1992 | Sherba | 424/36 |
| 5,208,016 | 5/1993 | Ohmae et al. | 424/78.27 |
| 5,209,922 | 5/1993 | Merianos et al. | 424/46 |
| 5,242,684 | 9/1993 | Merianos | 424/78.07 |
| 5,298,242 | 3/1994 | Vanlerberghe et al. | 424/78.36 |
| 5,300,287 | 4/1994 | Park | 424/78.04 |
| 5,348,738 | 9/1994 | Takatsuka et al. | 424/78.37 |
| 5,358,688 | 10/1994 | Robertson | 422/28 |
| 5,536,494 | 7/1996 | Park | 424/78.04 |

FOREIGN PATENT DOCUMENTS

| | | |
|---|---|---|
| 0 042 075 | 12/1981 | European Pat. Off. . |
| 0 554 029 | 8/1993 | European Pat. Off. . |
| 2 424 290 | 11/1979 | France . |
| 1 508 215 | 4/1978 | United Kingdom . |
| 83/01002 | 3/1983 | WIPO . |
| 90/09405 | 8/1990 | WIPO . |
| 95/30425 | 11/1995 | WIPO . |

OTHER PUBLICATIONS

Mammen, M., et al., "Effective Inhibitors of Hemagglutination by Influenza Virus Synthesized from Polymers Having Active Ester Groups. Insight into Mechanism of Inhibition," *J. Med. Chem.* (38):4179–4190 (1995).

Zlochevskaya, I.V., et al., "Effect of Polyethyleneimine on Certain Fungi," *Mosk. Univ. Biol. Sci. Bull.* 30(3–4):49–52 (1975).

Zalesov, V.S., et al., "Study of the Toxicity Physiological Effect and Antibacterial Activity of Polyethyleneimine," *Nauchn. Tr. Permsk. Farm. Instit.* (4):31–35 (1971). Abstract.

Tashiro, T., "Removal of *Escherichia coli* from Water by Systems Based on Insoluble Polystyrene–Poly (ethylene Glycol)s, –Polyethylenimines, and –Polyethylenepolyamines Quaternized," *J. Polymer Sci.* (34):1369–1377 (1991).

Haynie, S. L., et al., "Antimicrobial Activities of Amphiphilic Peptides Covalently Bonded to a Water–Insoluble Resin", *Antimicrob. Agents Chemotherapy*, 39(2): 301–307 (1995).

Maloy, W. L. and Kari, U. P., "Structure–Activity Studies on Magainins and Other Host Defense Peptides", *Biopolymers* (*Peptide Science*) 37: 105–122 (1995).

Arrowood, M. J., et al., "Hemolytic Properties of Lytic Peptides Active Against the Sporozoites of *Cryptosporidium parvum*", *J. Protozool.* 38(6): 161S–163S (1991).

*Primary Examiner*—D. Margaret M. Mach
*Attorney, Agent, or Firm*—Hamilton, Brook, Smith & Reynolds, P.C.

[57] ABSTRACT

A method for treating a microbial infection in a mammal, such as a human, comprising treating the mammal with a therapeutically effective amount of a polymer comprising an amino group or an ammonium group attached to the polymer backbone via an aliphatic spacer group. The polymer can be a homopolymer or a copolymer. In one embodiment, the polymer is a copolymer comprising a monomer having a pendant ammonium group and a hydrophobic monomer.

9 Claims, No Drawings

IONIC POLYMERS AS ANTI-INFECTIVE AGENTS

GOVERNMENT SUPPORT

The invention described herein was supported in whole or in part by Advanced Technology Program Cooperative Agreement No. 70NANB5H1063 from the National Institute of Standards and Technology. The United States Government has certain rights in the invention.

BACKGROUND OF THE INVENTION

A number of short (ca. 50 amino acid residues or fewer) linear or cyclic cytotoxic peptides have been isolated recently from a variety of sources. These include mellitin, from bee venom, the magainins, from frog skin, and cecropins, from insects (Maloy, et al., *Biopolymers* (*Peptide Science*) 37 : 105–122 (1995)). Although of widely varying peptide sequences and structures, these peptides all contain multiple lysine and arginine residues, and, at physiological pH, carry a net positive charge. They also form amphipathic structures wherein one portion of the structure is hydrophilic while the other portion is hydrophobic.

The peptides appear to act solely by direct lysis of the cell membrane (Maloy et al., supra (1995)). In the current model, cell lysis is initiated by the electrostatic attraction of the positive charge on the peptide to the negative phosphate head groups at the exterior surface of the membrane phospholipid bilayer. This interaction leads to insertion of the hydrophobic portion of the protein into the membrane, thereby disrupting the membrane structure. The lytic peptides are, in general, more active against prokaryotic cells, such as bacteria and fungi, than eukaryotic cells. This has led to interest in these peptides as potential agents for the treatment of infections in humans (Maloy et al., supra (1995); Arrowood et al., *J. Protozool.* 38 : 161S–163S (1991); Haynie et al., *Antimicrob. Agents Chemotherapy* 39 : 301–307 (1995).

The natural cytotoxic peptides, however, suffer from several disadvantages with respect to their use as human therapeutic agents. First, it appears that these peptides have evolved to act at high concentration at specific localized sites. Thus, when administered as a drug, the dosage necessary to attain an effective concentration at site of infection can be prohibitively high. A second disadvantage is the difficulty of isolating useful amounts of these peptides from the natural sources, along with the high cost of synthesizing useful amounts of peptides in this size regime. Finally, these compounds, like other peptides, are degraded in the gastrointestinal tract, and, thus, cannot be administered orally.

There is a need for anti-microbial agents which possess the broad activity spectrum of the natural cytotoxic peptides, but are inexpensive to produce, can be administered orally and have lower concentration requirements for therapeutic activity.

SUMMARY OF THE INVENTION

One aspect of the present invention is a method for treating a microbial infection in a mammal, comprising administering to the mammal a therapeutically effective amount of a polymer having an amine or ammonium group connected to the polymer backbone by an aliphatic spacer group.

The polymer to be administered can be a homopolymer or a copolymer. In one embodiment, the polymer further includes a monomer comprising a hydrophobic group, such as an aryl group or a normal or branched $C_3$–$C_{18}$-alkyl group.

The polymer to be administered can, optionally, further include a monomer comprising a neutral hydrophilic group, such as a hydroxyl group or an amide group.

Another aspect of the invention is a method for treating a microbial infection in a mammal, such as a human, comprising administering to the mammal a therapeutically effective amount of a polymer comprising a polymethylene backbone which is interrupted at one or more points by a quaternary ammonium group.

The present method has several advantages. For example, the polymers employed are easily prepared using standard techniques of polymer synthesis and inexpensive starting materials. The polymers will not be substantially degraded in the digestive tract and, therefore, can be administered orally. Polymer compositions can also be readily varied, to optimize properties such as solubility or water swellability and antimicrobial activity. Finally, the polymers to be administered include amine or ammonium functional groups attached to the polymer backbone via aliphatic spacer groups. The structural flexibility of such spacer groups minimizes backbone constraints on the interaction of the ammonium groups with anionic targets.

DETAILED DESCRIPTION OF THE INVENTION

The present invention relates to a method for preventing or treating a microbial infection in a mammal, such as a human, by administering to the mammal a therapeutically effective amount of a polymer comprising a plurality of amino or ammonium groups which are attached to the polymer backbone via aliphatic spacer groups.

As used herein, a "therapeutically effective amount" is an amount sufficient to inhibit, partially or totally, a microbial infection or to reverse development of a microbial infection or prevent or reduce its further progression. The term "polymer" refers to a macromolecule comprising a plurality of repeat units or monomers. The term includes homopolymers, which are formed from a singly type of monomer, and copolymers, which are formed of two or more different monomers. A "terpolymer" is a copolymer formed from three different monomers. The term polymer, as used herein, is intended to exclude proteins, peptides, polypeptides and proteinaceous materials.

As used herein, the term "polymer backbone" or "backbone" refers to that portion of the polymer which is a continuous chain, comprising the bonds which are formed between monomers upon polymerization. The composition of the polymer backbone can be described in terms of the identity of the monomers from which it is formed, without regard to the composition of branches, or side chains, off of the polymer backbone. Thus, a poly(acrylamide) polymer is said to have a poly(acrylamide) backbone, without regard to the substituents on the acrylamide nitrogen atom, which are components of the polymer side chains. A poly(acrylamide-co-styrene) copolymer, for example, is said to have a mixed acrylamide/styrene backbone.

The term "polymer side chain" or "side chain" refers to the portion of a monomer which, following polymerization, forms a branch off of the polymer backbone. In a homopolymer all of the polymer side chains are identical. A copolymer can comprise two or more distinct side chains. When a side chain comprises an ionic unit, for example, the ionic unit depends from, or is a substituent of, the polymer backbone, and is referred to as a "pendant ionic unit". The term "spacer group", as used herein, refers to a polyvalent molecular fragment which is a component of a polymer side chain and connects a pendant moiety to the polymer backbone. The term "aliphatic spacer group" refers to a spacer group which does not include an aromatic unit, such as a phenylene unit.

The term "addition polymer", as used herein, is a polymer formed by the addition of monomers without the consequent release of a small molecule. A common type of addition polymer is formed by polymerizing olefinic monomers, wherein monomers are joined by the formation of a carbon-carbon bonds between monomers, without the loss of any atoms which compose the unreacted monomers.

The term "monomer", as used herein, refers to both (a) a single molecule comprising one or more polymerizable functional groups prior to or following polymerization, and (b) a repeat unit of a polymer. An unpolymerized monomer capable of addition polymerization, can, for example, comprise an olefinic bond which is lost upon polymerization.

The quantity of a given polymer to be administered will be determined on an individual basis and will be determined, at least in part, by consideration of the individual's size, the severity of symptoms to be treated and the result sought. The polymer can be administered alone or in a pharmaceutical composition comprising the polymer, an acceptable carrier or diluent and, optionally, one or more additional drugs.

The polymers can be administered, for example, topically, orally, intranasally, or rectally. The form in which the agent is administered, for example, powder, tablet, capsule, solution, or emulsion, depends in part on the route by which it is administered. The therapeutically effective amount can be administered in a series of doses separated by appropriate time intervals, such as hours.

Microbial infections which can be treated or prevented by the method of the present invention include bacterial infections, such as infection by Streptococcus, including *Streptococcus mutans, Streptococcus salivarius*, and *Streptococcus sanguis*, Salmonella, Campylobacter, including *Campylobacter sputum*, Antinomyces, including *Actinomyces naeslundii* and *Actinomyces viscosus, Escherichia coli, Clostridium difficile*, Staphylococcus, including *S. aureus*, Shigella, Pseudomonas, including *P. aeruginosa, Eikenella corrodens, Actinobacillus actinomycetemcomitans, Bacteroides gingivalis*, Capnocytophaga, including *Capnocytophaga gingivalis, Wolinell recta, Bacteriodes intermedius*, Mycoplasma, including *Mycoplasma salivarium*, Treponema, including *Treponema denticola, Peptostreptococcus micros, Bacteriodes forsythus*, Fusobacteria, including *Fusobacterium nucleatum, Selenomonas sputigena, Bacteriodes fragilis, Enterobacter cloacae* and Pneumocystis. Also included are protozoal infections, such as infection by *Cryptosporidium parvum* and *Giardia lamblia*; ameobic infections, such as infection by *Entameoba histolytica* or Acanthameoba; fungal infections, such as infections by *Candida albicans* and *Aspergillus fumigatus*, and parasitic infections, such as infections by *A. castellani* and *Trichinella spiralis*. The method is useful for treating infections of various organs of the body, but is particularly useful for infections of the skin and gastrointestinal tract.

Polymers which are particularly suitable for the present method include polymers which can possess key characteristics of naturally occurring cytotoxic peptides, in particular, the ability to form amphipathic structures. The term "amphipathic", as used herein, describes a three-dimensional structure having discrete hydrophobic and hydrophilic regions. Thus, one portion of the structure interacts favorably with aqueous and other polar media, while another portion of the structure interacts favorably with non-polar media. An amphipathic polymer results from the presence of both hydrophilic and hydrophobic structural elements along the polymer backbone.

In one embodiment, the polymer to be administered polymer comprises a monomer of Formula I,

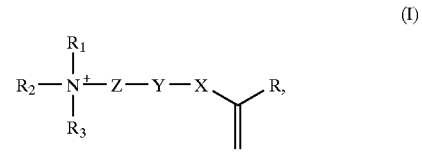

(I)

wherein X is a covalent bond, a carbonyl group or a $CH_2$ group, Y is an oxygen atom, an NH group or a $CH_2$ group, Z is an spacer group, R is a hydrogen atom or a methyl or ethyl group, $R_1$, $R_2$ and $R_3$ are each, independently, a hydrogen atom, a normal or branched, substituted or unsubstituted $C_1$–$C_{18}$-alkyl group, an aryl group or an arylalkyl group. Suitable alkyl substituents include halogen atoms, such as fluorine or chlorine atoms.

In the case in which at least one of $R_1$–$R_3$ is a hydrogen atom, the monomer can also exist in the free base, or amino form, that is, as the neutral conjugate base of the ammonium cation. The polymer comprising such a monomer can be administered in the protonated, cationic form, such as a salt of a pharmaceutically acceptable acid, or in the free base form. Suitable acids include hydrochloric acid, hydrobromic acid, citric acid, lactic acid, tartaric acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucoronic acid, oxalic acid, ascorbic acid, and acetylglycine. In either case, at physiological pH following administration, a plurality of amino groups will be protonated to become ammonium groups, and the polymer will carry an overall positive charge.

The spacer group is a component of the polymer side chain and connects the amino or ammonium group to the polymer backbone. The amino or ammonium group is, thus, a pendant group. The spacer group can be a normal or branched, saturated or unsaturated, substituted or unsubstituted alkylene group, such as a polymethylene group —$(CH_2)$—, wherein n is an integer from about 2 to about 15.

Suitable examples include the propylene, hexylene and octylene groups. The alkylene group can also, optionally, be interrupted at one or more points by a heteroatom, such as an oxygen, nitrogen (e.g, NH) or sulfur atom. Examples include the oxaalkylene groups —$(CH_2)_2O[(CH_2)_2O]_n(CH_2)_2$—, wherein n is an integer ranging from 0 to about 3.

Examples of monomers of Formula I having quaternary ammonium groups include 2-trimethylammoniumethylmethacrylate, 2-trimethylammoniumethylacrylate, N-(3-trimethylammoniumpropyl)methacrylamide, N-(6-trimethylammoniumhexyl)acrylamide, N-(3-trimethylammoniumpropyl)acrylamide, and N-(4-trimethylammoniumbutyl)allylamine, each of which also includes a counter anion. Examples monomers of Formula I having an amino group include allylamine and N-(3-dimethylaminopropyl)acrylamide.

Polymers to be administered which have quaternary ammonium groups or protonated amino groups will further comprise a pharmaceutically acceptable counter anion, such as anions which are conjugate bases of the pharmaceutically acceptable acids discussed above, for example, chloride, bromide, acetate, formate, citrate, ascorbate, sulfate or phosphate. The number of counter anions associated with the polymer prior to administration is the number necessary to balance the electrical charge on the polymer.

The polymer can also be a copolymer further comprising a hydrophobic monomer. The hydrophobic monomer can comprise a side chain bearing a hydrophobic group, such as a straight chain or branched, substituted or unsubstituted $C_3$–$C_{18}$-alkyl group or a substituted or unsubstituted aryl group. Examples of suitable hydrophobic monomers include styrene, N-isopropylacrylamide, N-t-butylacrylamide, N-n-butylacrylamide, heptafluorobutylacrylate, N-n-decylallylamine, N-n-decylacrylamide, pentafluorostyrene, n-butylacrylate, t-butylacrylate, n-decylacrylate, N-t-butylmethacrylamide, n-decylmethacrylate, and n-butylmethacrylate.

Examples of copolymers comprising a monomer of Formula I and a hydrophobic monomer include poly(N-(3-dimethylaminopropyl)acrylamide-co-N-(n-butyl)acrylamide) or salts thereof with pharmaceutically acceptable acids. Other examples of suitable copolymers include poly(2-trimethylammoniumethylmethacrylate-co-styrene) chloride, poly(2-trimethylammoniumethylmethacrylate-co-N-isopropylacrylamide) chloride, poly(2-trimethylammoniumethylmethacrylate-co-heptafluorobutylacryl) chloride, poly(3-trimethylammoniumpropylmethacrylate-co-styrene) chloride, poly(3-trimethylammoniumpropylmethacrylate-co-N-t-butylacrylamide) chloride, poly(3-trimethylammoniumpropylmethacrylate-co-N-n-butylacrylamide) chloride, and poly(N-(3-trimethylammoniumpropyl)allylamine-co-N-n-decylallylamine).

Each of these ionic copolymers can also be employed with counter ions other than chloride, for example, a conjugate base of a pharmaceutically acceptable acid.

In a further embodiment, the polymer to be administered comprises a monomer of Formula I, a hydrophobic monomer and a neutral hydrophilic monomer, such as acrylamide, methacrylamide, N-(2-hydroxyethyl)acrylamide or 2-hydroxyethylmethacrylate. Examples of polymers of this type include terpolymers of N-(3-trimethylammoniumpropyl)methacrylamide/N-isopropylacrylamide/2-hydroxyethylmethacrylate, N-(3-trimethylammoniumpropyl)methacrylamide/N-n-decylacrylamide/2-hydroxyethylmethacrylate, N-(3-trimethylammoniumpropyl)methacrylamide/N-t-butylmethacrylamide/methacrylamide, N-(3-trimethylammoniumpropyl)methacrylamide/n-decylacrylate/methacrylamide, 2-trimethylammoniumethylmethacrylate/n-butylacrylate/acrylamide, 2-trimethylammoniumethylmethacrylate/t-butylacrylate/acrylamide, 2-trimethylammoniumethylmethacrylate/n-decylacrylate/acrylamide, 2-trimethylammoniumethylmethacrylate/n-decylmethacrylate/methacrylamide, 2-trimethylammoniumethylmethacrylate/N-t-butyl methacrylamide/methacrylamide and 2-trimethylammoniumethylmethacrylate/N-n-butylmethacrylamide/methacrylamide.

The polymer to be administered can be an addition polymer having a polymer backbone such as a polyacrylate, polyacrylamide poly(allylalcohol), poly(vinylalcohol), poly(vinylamine), poly(allylamine), or polyalkyleneimine backbone. The polymer can have a uniform backbone if it is composed of monomers derived from a common polymerizable unit, such as acrylamide. If the polymer is a copolymer, it can also comprise a mixed backbone, for example, the monomer of Formula I can be an acrylamide derivative, while the hydrophobic monomer can be a styrene derivative. The polymers disclosed herein include examples of both uniform and mixed backbones.

The polymers of use in the present method also include condensation polymers, wherein polymerization of monomers is accompanied by the release of a small molecule, such as a water molecule. Such polymers include, for example, polyesters and polyurethanes.

The polymers of use in the present method are preferably substantially nonbiodegradable and nonabsorbale. That is, the polymers do not substantially break down under physiological conditions into fragments which are absorbable by body tissues. The polymers preferably have a nonhydrolyzable backbone, which is substantially inert under conditions encountered in the target reion of the body, such as the gastrointestinal tract.

The composition of the copolymers to be administered can vary substantially. The copolymer can comprise from about 95 mole percent to about 5 mole percent, preferably from about 20 mole percent to about 80 mole percent, of a monomer of Formula I. The copolymer can also comprise from about 95 mole percent to about 5 mole percent, preferably from about 20 mole percent to about 80 mole percent, of a hydrophobic monomer.

Other examples of polymers which are of use in the present method are disclosed in U.S. patent application Ser. Nos. 08/482,969, 08/258,477, 08/258,431, 08/469,659 and 08/471,769, the contents of each of which are incorporated herein by reference.

The polymer to be administered will, preferably, be of a molecular weight which is suitable for the intended mode of administration and allows the polymer to reach and remain within the targeted region of the body for a period of time sufficient to interact with the infecting organism. For example, a method for treating an intestinal infection should utilize a polymer of sufficiently high molecular weight to resist absorption, partially or completely, from the gastrointestinal tract into other parts of the body. The polymers can have molecular weights ranging from about 500 Daltons to about 500,000 Daltons, preferably from about 2,000 Daltons to about 150,000 Daltons.

The polymers which are useful in the present method can be prepared by known methods. A first method includes the direct polymerization of a monomer, such as trimethylammoniumethylacrylate chloride, or a set of two or more monomers, such as trimethylammoniumethyl-acrylate chloride, N-n-butylacrylamide and acrylamide. This can be accomplished via standard methods of free radical, cationic or anionic polymerization which are well known in the art. Due to reactivity differences between two monomers, the composition of a copolymer produced in this way can differ from the composition of the starting mixture. This reactivity difference can also result in a non-random distribution of monomers along the polymer chain.

A second method proceeds via the intermediacy of an activated polymer comprising labile side chains which are readily substituted by a desired side chain. An example of a suitable activated polymer is the succinimide ester of polyacrylic acid, poly(N-acryloyloxysuccinimide) (also referred to hereinafter as "pNAS"), which reacts with nucleophiles such as a primary amine to form a N-substituted polyacrylamide. Another suitable activated polymer is poly(para-nitrophenylacrylate), which react with amine nucleophiles in a similar fashion.

Polymers suitable for use in the present method can also be prepared by addition of a side chain to a preformed polymer. For example, poly(allylamine) can be alkylated at the amino nitrogen by one or more alkylating agents. For example, one fraction of amino groups can be alkylated using a normal or branched $C_3$–$C_{18}$-alkyl halide, such as n-decyl bromide, while another fraction can be alkylate by a quaternary ammonium-containing alkyl halide, such as 1-trimethylammonium-4-bromombutane.

A copolymer having a polyacrylamide backbone comprising amide nitrogens bearing two different substituents can be prepared by treating p(NAS) with less than one equivalent (relative to N-acryloyloxysuccinimide monomer) of a first primary amine, producing a poly(N-substituted acrylamide-co-N-acryoyloxysuccinimide) copolymer. Remaining N-acryoyloxysuccinimide monomer can then be reacted with, for example, an excess of a second primary amine to produce a polyacrylamide copolymer having two different N-substituents. A variety of copolymer compositions can, thus, be obtained by treating the activated polymer with different proportions of two or more amines.

An additional aspect of the present invention is a method for treating a microbial infection in a mammal, such as a human, comprising administering to the mammal a therapeutically effective amount of a polymer having an amino group or an ammonium group within the polymer backbone. The polymer can have, for example, a polymethylene backbone which is interrupted by one or more amino or ammonium groups. An example of a polymer of this type is poly(decamethylenedimethylammonium-co-ethylenedimethylammonium) bromide, which is synthesized via the reaction of N,N,N',N'-tetramethylethylenediamine and 1,10-dibromodecane. The polymer can also be administered in association with anions other than bromide, such as chloride or acetate anions. Other examples include poly(alkyleneimines), for example, poly(ethyleneimine). Such polymers can comprise secondary or tertiary amino groups, salts of such groups with pharmaceutically acceptable acids, and/or quaternary ammonium groups.

As discussed below in Example 35, several polymers described herein were tested for in vitro activity against cryptosporidium parvum infectivity in mammalian cell culture. Of these, poly(TMAEMC-co-styrene), described in Example 7, was most active, exhibiting greater than 90% inhibition of *C. parvum* infectivity relative to the control when applied as a 0.1 mg/mL solution in dimethylsulfoxide. The remaining polymers tested also showed significant anti-Cryptosporidium activity.

The invention will now be further and specifically described by the following examples.

EXAMPLES

The following abbreviations are used throughout the examples to denote the following monomers: MAPTAC, N-(3-trimethylammoniumpropyl)methacrylamide chloride; TMAEMC, 2-trimethylammoniumethylmethacrylate chloride; HEMA, 2-hydroxyethylmethacrylate; TMAEAC, 2-trimethylammoniumethylacrylate chloride.

The copolymers and terpolymers of the following examples are given nominal compositions which correspond to the molar ratios of starting monomers in the copolymerization mixture.

Example 1

Synthesis of poly(N-acryloyloxysuccinimide) (pDNAS)

A solution of N-acryloyloxysuccinimide (25.0 g, 148 mmole) in 100 mL dry DMF was degassed by nitrogen purging and simultaneously heated to 60° C. To the reaction mixture was added azobisisobutyronitrile (AIBN) (120 mg, 0.005 equivalents with respect to monomer). The reaction was allowed to proceed for 24 hours at 60° C. The polymer solution was cooled to room temperature and poured into rapidly stirred THF. The resulting white precipitate was filtered, washed with THF and dried in vacuo.

Example 2

Synthesis of poly(N-(3-dimethylamino-propyl)acrylamide-co-N-n-butylacrylamide)

To a solution of 3.0 g (17.75 mmole) pNAS in 20 mL dry DMF was added 0.6 g (3.55 mmole) n-butylamine. The resulting solution was stirred at room temperature for 14 hours, and then heated at 60° C. for 4 hours. After the solution was cooled to room temperature, 9.05 g (89 mmole) 3-dimethylaminopropylamine was added, and the resulting solution was stirred at room temperature for 2 hours, then heated to 60° C. for 20 hours. After cooling to room temperature, the solution was diluted with 25 mL water, and dialyzed against water for 24 hours. The solution was then lyophilized to afford poly(N-(3-dimethylaminopropyl-acrylamide)-co-N-n-butylacrylamide) as a tacky white solid.

Example 3

Synthesis of poly(N-(3-trimethylammoniumpropyl acrylamide-co-N-n-butylacrylamide) iodide To a suspension of poly(3-dimethylaminopropylacrylamide-co-N-n-butylacrylamide in methanol was added 0.5 g methyl iodide. The resulting mixture was stirred for 3 hours, and gradually became homogeneous. After stirring for another 12 hours, the solvent was removed under reduced pressure and the polymer was washed with dry hexane.

Example 4

Synthesis of poly(N-(2-hydroxyethyl)acrylamide-co-N-(6-trimethylammoniumhexyl)acrylamide) bromide To a solution of 2.48 g (15 mmole) pNAS in 5 mL DMF was added 1.00 g (3 mmole) 1-trimethylammonium-6-hexanamine bromide. The solution was stirred at room temperature for 4 hours and then heated at 60° C. for 20 hours. The solution was cooled to room temperature, and then 8.95 g (150 mmole) 2-ethanolamine was added. The resulting mixture was heated to 80° C. for 20 hours, cooled to room temperature and diluted with 10 mL water. The solution was dialyzed against water for 24 hours, then lyophilized, yielding the polymer as a brittle white solid.

Example 5

Synthesis of poly(TMAEAC)

A solution of 48.25 g (0.25 mol) 2-trimethylammoniumethylacrylate chloride in 400 mL isopropanol was degassed by nitrogen purging and heated to 35° C. To this stirred solution was added a solution of 0.8 g potassium persulfate in 10 mL distilled water. A slight exotherm was observed. The solution was stirred at 35° C. for 6 hours, then cooled to room temperature. The solution was added to hexanes and the resulting precipitate was isolated by filtration.

Example 6

Synthesis of poly(decamethylenedimethylammonium-co-ethylenedimethylammonium) bromide N,N,N'N'-tetramethylethylenediamine (10.0 g, Aldrich), 1,10-dibromodecane (25.8 g, Aldrich) and methanol (100 mL) were placed into a three-neck 250 mL round bottom flask. The mixture was heated with gentle stirring to 65° C.

for 6 days, at which point methanol (40 mL) was added, and the mixture was refluxed for an additional 2 days. The mixture was then dripped into acetone, forming a solid that was collected by filtration, rinsed with acetone, and dried in a vacuum oven to yield 30.9 g of product.

Example 7
Synthesis of poly(TMAEMC-co-styrene) 75/25

A 500 mL round bottomed flask was charged with trimethylammoniumethylmethacrylate chloride (26.0 g of a 70wt % aqueous solution, 18.2 g), styrene (6.0 g) and isopropanol (150 mL). The solution was degassed by the addition of a rapid stream of nitrogen for 10 minutes, followed by the addition of AIBN (0.5 g). The solution was degassed for a further thirty minutes and, while continuing the addition of nitrogen, the solution was heated to 70° C., and the temperature maintained for 17 h. The polymer began to precipitate within 2 h, and by the completion of the reaction a sticky white precipitate had formed. The reaction mixture was cooled, the isopropanol was decanted from the polymer, and the polymer was dissolved in methanol. Dropwise addition of the methanol solution to ethyl acetate (1200 mL) caused the polymer to precipitate as a fine white powder which was recovered by filtration.

Example 8
Synthesis of Poly(TMAEMC-co-N-isopropylacrylamide) (67/33)

A 500 mL round bottomed flask was charged with trimethylammoniumethylmethacrylate chloride (14.5 g of a 70wt % aqueous solution, 10.0 g), N-isopropylacrylamide (5.0 g) and isopropanol (150 mL). The solution was degassed by the addition of a rapid stream of nitrogen for 10 minutes, followed by the addition of AIBN (0.5 g). The solution was degassed for a further 60 minutes. The reaction mixture was heated to 70° C., and the temperature maintained for 16 h. The polymer partially precipitated over the course of the reaction. Upon cooling, the propanol was decanted from the polymer, and the polymer was dissolved in methanol.

Precipitation of the methanol solution dropwise into ethyl acetate (1200 mL) caused the polymer to be deposited as white curds which were recovered by filtration, washed with ethyl acetate, and dried in vacuo.

Additional TMAEMC/N-isopropylacrylamide copolymers were prepared by a similar method with the starting monomers in the following ratios:

TMAEMC/N-isopropylacrylamide=40/60, 25/75 and 15/85.

Example 9

Synthesis of poly(MAPTAC-co-styrene) 75/25

To isopropanol (150 mL) was added a solution of N-(3-trimethylammoniumpropyl)methacrylamide chloride in water (50 wt % solution, 24.0 g, 12.0 g of monomer). To this solution was added styrene (6.0 g), followed by the addition of AIBN (0.5 g). The homogeneous solution was degassed by bubbling a stream of nitrogen through it for 30 minutes. The solution was heated to 70° C. for 15 h. The polymer partially precipitated as the reaction proceeded. The solution was cooled, the isopropanol was decanted off, the white solid was washed with propanol (50 mL). The propanol was decanted a second time, and the solid was dissolved in methanol (150 mL). The clear solution was added dropwise to ethyl acetate, causing the polymer to be precipitated as a white powder. The polymer was recovered by filtration, washed with 50 mL of ethylacetate and air dried.

An additional MAPTAC/styrene copolymer was prepared by a similar method employing a 50/50 mixture of starting monomers.

Example 10
Synthesis of poly(TMAEMC-co-heptafluorobutylacrylate) 75/25

A 500 mL round bottomed flask was charged with 2-trimethylammoniumethylmethacrylate chloride (26.0 g of a 70wt % aqueous solution, 18.2 g), heptafluorobutylacrylate (6.0 g) and isopropanol (150 mL). The solution was degassed by the addition of a rapid stream of nitrogen for 10 minutes, followed by the addition of AIBN (0.5 g). The solution was degassed for a further thirty minutes and, continuing the addition of nitrogen, the solution was heated to 70° C. The temperature was maintained for 17 h. The polymer began to precipitate within 1 h, and by the completion of the reaction a sticky white precipitate had formed. The reaction mixture was cooled, the propanol was decanted from the polymer, and the polymer was dissolved in methanol (100 mL). Precipitation of the methanol solution dropwise into ethyl acetate (1200 mL) caused the polymer to be deposited as a white solid which was recovered by filtration.

Example 11

Synthesis of poly(MAPTAC-co-N-t-butylacrylamide) 75/25

To a 500 mL round-bottom, three-neck flask fitted with a thermocouple, reflux condenser, and septum was added 36.4 g of a 50% aqueous solution of N-(3-trimethylammoniumpropyl)methacrylamide chloride and 6 g of N-t-butylacrylamide followed by 150 mL of isopropanol. The solution was purged with nitrogen for 1 hour and 0.5 g AIBN was added. The mixture was purged for ~15 minutes until all of the AIBN dissolved. The solution was heated to 75° C. under nitrogen for 16 hours.

The resulting reaction mixture consisted of two phases. The turbid liquid phase was decanted from the bulk of the reaction which was a white sticky solid phase. The liquid was precipitated into 1200 mL of ethyl acetate and filtered by vacuum filtration through a Buchner funnel.

The white hygroscopic precipitate was dried in vacuo. The solid phase was dissolved in methanol and precipitated into 1200 mL of ethyl acetate and filtered by vacuum filtration to yield a white powder which was stored under vacuum.

Additional MAPTAC/N-t-butylacrylamide copolymers were prepared by a similar method beginning with the starting monomers in the following ratios: N-(3-trimethylammoniumpropyl)methacrylamide/N-t-butylacrylamide=60/40, 50/50, 40/60, and 25/75.

Example 12

Synthesis of poly(N-decylallylamine-co-N-(4-trimethylammoniumbutyl)allylamine)

To a solution of poly(allylamine).HCl (20.15 g of a 50 wt % aqueous solution) was added sodium hydroxide (5.64 g as a solid. The solution was stirred for 40 minutes, filtered and the filter cake was washed with methanol (15 mL). The solution was further diluted with methanol (25 mL) and to the solution was added 1-bromodecane (7.73 g, 35 mmol) and (1-trimethylamino-4-bromobutane) chloride (9.13 g, 35 mmol). A solution was prepared of sodium hydroxide (2.8 g, 70 mmol) in water (5 mL). This solution was added to the reaction mixture in four portions at thirty minute intervals. The solution was then stirred at room temperature for 24 h, followed by dialysis against deionized water and freeze-dried. A total of 23.2 g of a glassy, hygroscopic solid was recovered.

Example 13
Synthesis of poly(TMAEMC-co-N-t-butylacrylamide) 57/43

To a 500 mL round-bottom, three-neck flask fitted with a thermocouple, reflux condenser, and septum was added 18.20 g of a 70% aqueous solution of 2-trimethylammoniumethylmethacrylic chloride and 9.7 g of N-t-butylacrylamide followed by 150 mL of isopropanol. The solution was purged with nitrogen for 1 hour and 0.5 g AIBN was added. The mixture was purged for ~15 minutes until all of the AIBN dissolved. The solution was heated to 75° C. under nitrogen for 16 hours.

The resulting reaction mixture consisted of two easily separable phases. The liquid phase was decanted from the bulk of the reaction which was a white solid. The liquid was precipitated into 1200 mL of ethyl acetate and filtered by vacuum filtration through a Buchner funnel. The white precipitate was dried in vacuo and weighed: fraction A, 10.1 g (45.1% yield based on 22.4 g monomers added). The solid phase was dissolved in methanol and precipitated into 600 mL of ethyl acetate and filtered by vacuum filtration to yield fraction B, 5.81 g of a white powder (25.9% yield) which was dried under vacuum.

TMAEMC/N-t-Butylacrylamide copolymers were also prepared by a similar method with the starting monomers in the following ratios: TMAEMC/N-t-Butylacrylamide=63/37, 50/50, 40/60, 25/75, 15/85 and 5/95.

Example 14

Synthesis of poly(MAPTAC-co-N-n-decylacrylamide) 75/25

To a 500 mL round-bottom, three-neck flask fitted with a thermocouple, reflux condenser, and septum was added 36.4 g of a 50% aqueous solution of N-(3-trimethylammoniumpropyl)methacrylamide chloride and 6 g of N-n-decylacrylamide followed by 150 mL of isopropanol. The solution was purged with nitrogen for 1 hour and 0.5 g AIBN was added. The mixture was purged for ~15 minutes until all of the AIBN dissolved. The solution was heated to 75° C under nitrogen for 16 hours.

The reaction mixture consisted of two easily separable phases. The clear, yellow liquid phase was precipitated into 1200 mL of ethyl acetate. The precipitate was isolated by filtration and dried under vacuum to yield 2.14 g of a yellow powder, fraction A (8.84% yield). Methanol was added to the creamy yellow reaction precipitate and the resulting turbid yellow solution was precipitated into 1200 mL of ethyl acetate. The white precipitate was isolated by filtration and dried under vacuum to yield fraction B, 17.22 g, as a slightly yellow powder (71.2% yield).

Additional MAPTAC/N-n-decylacrylamide copolymers were prepared by a similar method with the starting monomers in the following ratios: MAPTAC/N-n-decylacrylamide=60/40, 50/50, and 40/60.

Example 15
Synthesis of poly(TMAEMC-co-pentafluorostyrene) 75/25

To a 500 mL round-bottom, three-neck flask fitted with a thermocouple, reflux condenser, and septum was added 26.0 g of a 70% aqueous solution of 2-trimethylammoniumethylmethacrylate chloride and 6 g of pentafluorostyrene followed by 150 mL of isopropanol. The solution was purged with nitrogen for 1 hour and 0.5 g AIBN was added. The mixture was purged for ~15 minutes until all of the AIBN dissolved. The solution was heated to 75° C. under nitrogen for 16 hours.

The reaction mixture consisted of two phases. The turbid solution was discarded. The bulk of the reaction, consisting of a white solid mass at the bottom of the flask, was dissolved in methanol. The resulting clear solution was precipitated into 1200 mL of ethyl acetate. The white precipitate was isolated by vacuum filtration to yield 20.39 g of a fine white powder (84.3% yield).

Additional TMAEMC/pentafluorostyrene copolymers were prepared by a similar method with the starting monomers in the following ratios: TMAEMC/pentafluorostyrene=60/40 and 50/50.

Example 16
Synthesis of poly(MAPTAC-co-pentafluorostyrene) 75/25

To a 500 mL round-bottom, three-neck flask fitted with a thermocouple, reflux condenser, and septum was added 36.3 g of a 50% aqueous solution of N-(3-trimethylammoniumpropyl)methacrylamide chloride and 6 g of pentafluorostyrene followed by 150 mL of isopropanol. The solution was purged with nitrogen for 1 hour and 0.5 g AIBN was added. The mixture was purged for ~15 minutes until all of the AIBN dissolved. The solution was heated to 75 ° C. under nitrogen for 16 hours.

The reaction mixture consisted of a turbid solution with a white precipitate. The supernatent was disgarded. The white reaction precipitate was dissolved in methanol and the resulting clear solution was precipitated into 1200 mL of ethyl acetate. The white precipitate was isolated by filtration and dried under vacuum to yield 12.81 g of a fine white powder (52.9% yield).

Additional MAPTAC/pentafluorostyrene copolymers were prepared by a similar method with the starting monomers in the following ratios: MAPTAC/pentafluorostyrene= 60/40 and 50/50.

Example 17
Synthesis of MAPTAC/N-t-Butylacrylamide/HEMA Terpolymer 33/33/33

To a 500 mL round-bottom, three-neck flask fitted with a thermocouple, reflux condenser, and septum was added 150 mL of isopropanol followed by 16.1 g of a 50% aqueous solution of N-(3-trimethylammoniumpropyl) methacrylamide chloride, 8 g of N-t-butylacrylamide, and 8 g of 2-hydroxyethylmethacrylate. The solution was purged with nitrogen for 1 hour and 0.5 g of AIBN was added. The mixture was purged for ~15 min until all of the AIBN dissolved. The solution was heated to 75° C. under nitrogen for 16 hours.

The reaction mixture consisted of a turbid solution with a white latex in the bottom of the flask. The solution was precipitated into 1200 mL of ethyl acetate. The white precipitate was isolated by filtration to yield a sticky white powder which was dried under vacuum to yield 10.43 g of a lumpy white solid (fraction A) (43.1% yield). The white reaction precipitate was dissolved in methanol and precipitated into 1200 mL of ethyl acetate. The precipitate was isolated by filtration and dried under vacuum to yield 8.89 g of a fine white powder (fraction B) (36.7% yield).

Additional MAPTAC/N-t-butylacrylamide/HEMA terpolymers were prepared by a similar method beginning with the following ratios of the starting monomers: MAPTAC/N-t-Butylacrylamide/HEMA=28/43/28, 23/53/23, and 18/63/18.

Example 18
Synthesis of MAPTAC/N-Isopropylacrylamide/HEMA Terpolymer 18/63118

To a 500 mL round-bottom, three-neck flask fitted with a thermocouple, reflux condenser, and septum was added 150 mL of isopropanol followed by 8.9 g of a 50% aqueous solution of N-(3-trimethylammoniumpropyl) methacrylamide chloride, 15.3 g of N-iso-propylacrylamide, and 4.4 g of 2-hydroxyethylmethacrylate. The solution was purged with nitrogen for 1 hour and 0.5 g of AIBN was added. The mixture was purged for ~15 min until all of the AIBN dissolved. The solution was heated to 75° C. under nitrogen for 16 hours.

The clear slightly pink reaction solution was precipitated into 1200 mL of ethyl acetate. The precipitate was isolated by filtration to yield a sticky white solid which was dried under vacuum to yield 14.42 g of a hard clear/white granular solid (59.6% yield).

Example 19
Synthesis of MAPTAC/N-Decylacrylamide/HEMA Terpolymer 33/33/33

To a 500 mL round-bottom, three-neck flask fitted with a thermocouple, reflux condenser, and septum was added 150 mL of isopropanol followed by 16.1 g of a 50% aqueous solution of N-(3-trimethylammoniumpropyl) methacrylamide chloride, 8 g of N-decylacrylamide, and 8 g of 2-hydroxyethylmethacrylate. The solution was purged with nitrogen for 1 hour and 0.5 g of AIBN was added. The mixture was purged for ~15 min until all of the AIBN dissolved. The solution was heated to 75° C. under nitrogen for 16 hours.

The reaction mixture consisted of two phases. The clear yellow solution was precipitated into 1200 mL of ethyl acetate. The precipitate was isolated by filtration. The sticky yellow precipitate was dried under vacuum and the resulting brittle clear yellow foam was crushed to yield 4.98 g of a fine yellow granular powder (fraction A) (20.6% yield). The white reaction latex was dissolved in methanol and precipitated into 1200 mL of ethyl acetate. The precipitate was isolated by filtration and dried under vacuum to yield 10.24 g of a slightly yellow granular solid (fraction B) (42.3% yield).

Additional MAPTAC/N-Decylacrylamide/HEMA terpolymers were prepared by a similar method beginning with the following ratios of starting monomers: MAPTAC/N-Decylacrylamide/HEMA=28/43/28, 23/53/23, and 18/63/18.

Example 20
Synthesis of TMAEAC/n-Butylacrylate/Acrylamide Terpolymer 10/30/60

To a 500 mL round-bottom, three-neck flask fitted with a thermocouple, reflux condenser, and septum was added 150 mL of isopropanol followed by 4.84 g of a 50% aqueous solution of 2-trimethylammoniumethylacrylate chloride, 7.26 g of n-butylacrylate, and 14.52 g of acrylamide. The solution was purged with nitrogen for 1 hour and 0.5 g AIBN was added. The mixture was purged for ~15 minutes until all of the AIBN dissolved. The solution was heated to 75 ° C. under nitrogen for 16 hours.

The resulting white reaction mixture was filtered by vacuum filtration through a Buchner funnel to yield a white powder. The powder was washed with isopropanol and dried under vacuum to yield 21.57 g of a fine white powder (89.1% yield based on 24.2 g of monomers).

Additional TMAEAC/n-butylacrylate/acrylamide terpolymers were prepared by a similar method beginning with the following ratios of starting monomers: TMAEMC/n-butylacrylate/acrylamide=20/20/60 and 30/10/60.

Example 21
Synthesis of TMAEAC/t-Butylacrylate/Acrylamide Terpolymer 10/30/60

To a 500 mL round-bottom, three-neck flask fitted with a thermocouple, reflux condenser, and septum was added 150 mL of isopropanol followed by 4.84 g of a 50% aqueous solution of 2-trimethylammoniumethylacrylate chloride, 7.26 g of t-butylacrylate, and 14.52 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The resulting white reaction mixture was filtered by vacuum filtration through a Buchner funnel to yield a white powder. The powder was washed with isopropanol and dried under vacuum to yield 21.13 g of a white powder (87.3% yield).

Additional TMAEAC/t-butylacrylate /acrylamide terpolymers were prepared by a similar method beginning with the following ratios of starting monomers: TMAEAC/t-butylacrylate/acrylamide=20/20/60 and 30/10/60.

Example 22
Synthesis of TMAEAC/n-Decylacrylate/Acrylamide Terpolymer 10/30/60

To a 500 mL round-bottom, three-neck flask fitted with a thermocouple, reflux condenser, and septum was added 150 mL of isopropanol followed by 4.84 g of a 50% aqueous solution of 2-trimethylammoniumethylacrylate chloride, 7.26 g of n-decylacrylate, and 14.52 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The resulting white reaction mixture was filtered by vacuum filtration through a Buchner funnel to yield a white powder. The powder was washed with isopropanol and dried under vacuum to yield 21.52 g of a fine white powder (89% yield).

Additional TMAEAC/n-decylacrylate /acrylamide terpolymers were prepared by a similar method beginning with the following ratios of starting monomers: TMAEAC/n-decylacrylate/acrylamide=20/20/60, and 30/10/60.

Example 23
Synthesis of MAPTAC/N-t-Butylmethacrylamide/Methacrylamide Terpolymer 10/30/60

To a 500 mL round-bottom, three-neck flask fitted with a thermocouple, reflux condenser, and septum was added 150 mL of isopropanol followed by 4.84 g of a 50% aqueous solution of N-(3-trimethylammoniumpropyl) methacrylamide chloride, 7.26 g of N-t-butylmethacrylamide, and 14.52 g of methacrylamide. The solution was purged with nitrogen for 1 hour and 0.5 g of AIBN was added. The mixture was purged for ~15 min until all of the AIBN dissolved. The solution was heated to 75° C. under nitrogen for 16 hours.

The white reaction mixture was too difficult to filter by vacuum filtration so centrifugation techniques were employed instead. The reaction mixture was poured into 50 mL centrifuge tubes and centrifuged. The supernatant was discarded. Isopropanol was added to the polymer and the mixture was stirred and centrifuged. The supernatant was discarded and the white solids were combined and dried under vacuum to yield 14.99 g of a slightly buff powder (61.9% yield).

Additional MAPTAC/N-t-butylmethacrylamide/methacrylamide terpolymers were prepared by a similar method beginning with the following ratios of starting monomers: MAPTAC/N-t-butylmethacrylamide/methacrylamide=20/20/60, 33/33/33 and 30/10/60.

Example 24
Synthesis of MAPTAC/n-Decylmethacrylate/Methacrylamide Terpolymer 10/30/60

To a 500 mL round-bottom, three-neck flask fitted with a thermocouple, reflux condenser, and septum was added 150 mL of isopropanol followed by 4.84 g of a 50% aqueous solution of N-(3-trimethylammoniumpropyl) methacrylamide chloride, 7.26 g of n-decylmethacrylate, and 14.52 g of methacrylamide. The solution was purged with nitrogen for 1 hour and 0.5 g of AIBN was added. The mixture was purged for ~15 min until all of the AIBN dissolved. The solution was heated to 75° C. under nitrogen for 16 hours.

The isopropanol was decanted leaving a white chunky powder. Isopropanol was added and the mixture was poured into 50 mL centrifuge tubes and centrifuged. The supernatant was discarded. Isopropanol was added to the polymer and the mixture was stirred and centrifuged. The supernatant was discarded and the white solids were combined and dried under vacuum to yield 18.50 g of a granular white solid (76.4% yield).

Additional MAPTAC/N-decylmethacrylamide/methacrylamide terpolymers were prepared by a similar method beginning with the following ratios of starting monomers: MAPTAC/N-decylmethacrylamide/methacrylamide=20/20/60, 33/33/33 and 30/10/60.

Example 25
Synthesis of TMAEMC/n-Decylmethacrylate/Methacrylamide Terpolymer 10/30/60

To a 500 mL round-bottom, three-neck flask fitted with a thermocouple, reflux condenser, and septum was added 150 mL of isopropanol followed by 3.46 g of a 70% aqueous solution of 2-trimethylammoniumethylmethacrylate chloride, 7.26 g of n-decylmethacrylate, and 14.52 g of methacrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The white reaction mixture was poured into 50 mL centrifuge tubes and centrifuged. The supernatant was discarded. Isopropanol was added to the polymer and the mixture was stirred and centrifuged. The supernatant was discarded and the white solids were combined and dried under vacuum to yield 10.29 g of a hard white solid (42.5% yield).

Additional TMAEMC/N-n-decylmethacrylamide/methacrylamide terpolymers were prepared by a similar method beginning with the following ratios of starting monomers: TMAEMC/N-n-decylmethacrylamide/methacrylamide 20/20/60, 33/33/33 and 30/10/60.

Example 26
Synthesis of TMAEMC/N-t-Butylmethacrylamide/Methacrylamide TerPolymer 10/30/60

To a 500 mL round-bottom, three-neck flask fitted with a thermocouple, reflux condenser, and septum was added 150 mL of isopropanol followed by 3.46 g of a 70% aqueous solution of 2-trimethylammoniumethylmethacrylate chloride, 7.26 g of N-t-butylmethacrylamide, and 14.52 g of methacrylamide. The solution was purged with nitrogen for 10 1 hour and 0.5 g AIBN was added. The mixture was purged for ~15 minutes until all of the AIBN dissolved. The solution was heated to 75° C. under nitrogen for 16 hours.

The white reaction mixture was poured into 50 mL centrifuge tubes and centrifuged. The supernatant was discarded. Isopropanol was added to the polymer and the mixture was stirred and centrifuged. The supernatant was discarded and the white solids were combined and dried under vacuum to yield 18.35 g of a fine white powder (75.8% yield).

Additional TMAEMC/N-t-butylmethacrylamide/methacrylamide terpolymers were prepared by a similar method beginning with the following ratios of starting monomers: TMAEMC/N-t-butylmethacrylamide/methacrylamide=20/20/60, 33/33/33 and 30/10/60.

Example 27
Synthesis of TMAEMC/n-Butylmethacrylate/Methacrylamide Terpolymer 10/30/60

To a 500 mL round-bottom, three-neck flask fitted with a thermocouple, reflux condenser, and septum was added 150 mL of isopropanol followed by 3.46 g of a 70% aqueous solution of 2-trimethylammoniumethylmethacrylate chloride, 7.26 g of n-butylmethacrylate, and 14.52 g of methacrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The white reaction mixture was poured into 50 mL centrifuge tubes and centrifuged. The supernatant was discarded. Isopropanol was added to the polymer and the mixture was stirred and centrifuged. The supernatant was discarded and the white solids were combined and dried under vacuum to yield 20.99 g of a clumpy white powder (86.7% yield).

Additional TMAEMC/N-n-butylmethacrylamide/methacrylamide terpolymers were prepared by a similar method beginning with the following ratios of starting monomers: TMAEMC/N-n-butylmethacrylamide/methacrylamide=20/20/60 and 30/10/60.

Example 28
Synthesis of MAPTAC/n-Butylmethacrylate/Methacrylamide Terpolymer 10/30/60

To a 500 mL round-bottom, three-neck flask fitted with a thermocouple, reflux condenser, and septum was added 150 mL of isopropanol followed by 4.84 g of a 50% aqueous solution of N-(3-trimethylammoniumpropyl) methacrylamide chloride, 7.26 g of n-butylmethacrylate, and 14.52 g of methacrylamide. The solution was purged with nitrogen for 1 hour and 0.5 g of AIBN was added. The mixture was purged for ~15 min until all of the AIBN dissolved. The solution was heated to 75° C. under nitrogen for 16 hours.

The white reaction mixture was filtered by vacuum filtration to yield a white powder. The powder was washed with isopropanol and dried under vacuum to yield 22.20 g of a white powder (91.7% yield).

Additional MAPTAC/n-butylmethacrylate/methacrylamide terpolymers were prepared by a similar method beginning with the following ratios of starting monomers: MAPTAC/n-butylmethacrylate/methacrylamide=20/20/60 and 30/10/60.

Example 29
Synthesis of TMAEAC/n-Decylacrylamide/Acrylamid Terpolymer 33/33/33

To a 500 mL round-bottom, three-neck flask fitted with a thermocouple, reflux condenser, and septum was added 150 mL of isopropanol followed by 16.13 g of a 50% aqueous solution of 2-trimethylammoniumethylacrylate chloride, 8.06 g of n-decylacrylamide, and 8.06 g of acrylamide. The solution was purged with nitrogen for 1 hour and 0.5 g AIBN was added. The mixture was purged for -15 minutes until all of the AIBN dissolved. The solution was heated to 75° C. under nitrogen for 16 hours.

The reaction mixture was precipitated into 1200 mL of ethyl acetate. The fine precipitate was filtered by vacuum filtration to yield a sticky yellow material. The light yellow solid was dissolved in methanol and precipitated into 1200 mL of ethyl acetate. The precipitate was filtered by vacuum filtration to yield 10.85 g of a sticky, slightly yellow powder (44.8% yield).

Example 30

Synthesis of TMAEAC/N-t-Butylacrylamide/Acrylamide Terpolymer 33/33/33

To a 500 mL round-bottom, three-neck flask fitted with a thermocouple, reflux condenser, and septum was added 150 mL of isopropanol followed by 16.13 g of a 50% aqueous solution of 2-trimethylammoniumethylacrylate chloride, 8.06 g of N-t-butylacrylamide, and 8.06 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The reaction mixture consisted of a clear colorless solution with a small amount of white sticky solid. The clear solution was precipitated into 1200 mL of ethyl acetate. The white precipitate was filtered, dissolved in water, and lyophilized to yield 6.65 of a white powder (27.5% yield).

Example 31

Synthesis of TMAEAC/Styrene/Acrylamide Terpolymer 33/33/33

To a 500 mL round-bottom, three-neck flask fitted with a thermocouple, reflux condenser, and septum was added 150 mL of isopropanol followed by 16.13 g of a 50% aqueous solution of 2-trimethylammoniumethylacrylate chloride, 8.06 g of styrene, and 8.06 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The reaction mixture consisted of a clear colorless solution and a white solid. The clear solution was disgarded. The solid was dissolved in methanol, and precipitated into ethyl acetate (1200 mL). A white precipitate formed which settled out of the solution as a sticky white solid. The ethyl acetate was decanted and the solid dried by passing nitrogen through the flask. The solid was dissolved in water and lyophilized to yield 18.14 g of a fine white powder (75% yield).

Example 32

Synthesis of TMAEAC/n-Butylacrylate/Acrylamide Terpolymer 33/33/33

To a 500 mL round-bottom, three-neck flask fitted with a thermocouple, reflux condenser, and septum was added 150 mL of isopropanol followed by 16.13 g of a 50% aqueous solution of 2-trimethylammoniumethylacrylate chloride, 8.06 g of n-butylacrylate, and 8.06 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The reaction mixture consisted of a clear colorless solution and a white chunky solid. The solution phase was disgarded and the white solid dissolved in water, filtered and lyophilized to yield 12.84 of a fine white powder (53.1% yield).

Example 33

Synthesis of TMAEAC/n-Decylacrylate/Acrylamide Terpolymer 33/33/33

To a 500 mL round-bottom, three-neck flask fitted with a thermocouple, reflux condenser, and septum was added 150 mL of isopropanol followed by 16.13 g of a 50% aqueous solution of 2-trimethylammoniumethylacrylate chloride, 8.06 g of n-decylacrylate, and 8.06 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The white reaction mixture was precipitated into 1200 mL of ethyl acetate. The turbid solution was decanted and the polymer was dried with nitrogen, dissolved in water, and lyophilized to yield 8.79 g of fine white powder (36.3% yield).

Example 34

Synthesis of TMAEAC/t-Butylacrylate/Acrylamide Terpolymer 33/33/33

To a 500 mL round-bottom, three-neck flask fitted with a thermocouple, reflux condenser, and septum was added 150 mL of isopropanol followed by 16.13 g of a 50% aqueous solution of 2-trimethylammoniumethylacrylate chloride, 8.06 g of t-butylacrylate, and 8.06 g of acrylamide. The solution was purged with nitrogen for 1 hour and 0.5 g AIBN was added. The mixture was purged for ~15 minutes until all of the AIBN dissolved. The solution was heated to 75° C. under nitrogen for 16 hours.

The white reaction mixture was precipitated into 1200 mL of ethyl acetate. The turbid solution was decanted and the polymer was dried with nitrogen, dissolved in water, and lyophilized to yield 6.51 g of fine white powder (26.9% yield).

Example 35

In vitro activity of selected polymers against C. Parvum infectivity

Confluent MDBK cell monolayers were grown on 16 well slides, and infected with $5 \times 10^5$ of C. parvum oocysts per well. Various dilutions of the test reagents in dimethylsulfoxide (DMSO) were added to the monolayers and cultures were incubated at 37° C.(8% $CO_2$) for 48 hours. The level of C. parvum infections was determined and analysed by an indirect immunofluorescence (IF) assay at 48 hours.

Anti-C. parvum sporozoite rabbit serum (1:1000) was used as the primary antibody, and fluorscein-conjugated anti rabbit goat serum (1:100) was used as the secondary antibody. Each dilution was tested in quadruple, and each assay was performed at least two times. The monolayers were methanol fixed and, after IF labelling, the number of parasites observed in 10 high power fields (HPF) per well in each of the four wells per dilution was counted, statistically analysed and compared with infected wells which contained DMSO only. Paromomycin was used as the positive control drug. The results are presented in the following Table.

TABLE

| Polymer | Concentration (mg/mL) | % Inhibition |
|---|---|---|
| poly (TMAEMC-co-styrene) 25/75, | 0.1 | 91.7 |
| Example 7 | 0.033 | 83.2 |
|  | 0.011 | 38.9 |
|  | 0.0037 | 3.95 |
| poly (TMAEMC-co-N-t-butylacrylamide), 15/85 | 10 | 100 |

TABLE-continued

| Polymer | Concentration (mg/mL) | % Inhibition |
|---|---|---|
| Example 13 | 1.0 | 100 |
|  | 0.1 | 59.1 |
|  | 0.01 | 38.0 |
| poly (MAPTAC-co-N-n-decylacrylamide), 40/60 | 10 | 100 |
| Example 14 | 1.0 | 100 |
|  | 0.1 | 64.3 |
|  | 0.01 | 35.5 |
| poly (MAPTAC-co-N-t-butylacrylamide-co-HEMA) 33/33/33 | 10 | 70.2 |
| Example 17 | 1.0 | 57.4 |
|  | 0.1 | 52.1 |
|  | 0.01 | 18.4 |
| Poly (TMAEMC-co-heptafluorobutylacrylate 60/40, | 0.1 | 91.35 |
| Example 10 | 0.033 | 53.0 |
|  | 0.011 | 23.5 |
|  | 0.0037 | 4.2 |
| paromomycin | 2 | 79.4 |

Equivalents

Those skilled in the art will recognize or be able to ascertain using no more than routine experimentation many equivalents to the specific embodiments of the invention described herein. Such equivalents are intended to be encompassed in the scope of the following claims.

We claim:

1. A method for treating a gastrointestinal infection in a mammal, comprising contacting the gastrointestinal tract of the mammal with a therapeutically effective amount of a polymer having an amino group or an ammonium group within the polyner backbone.

2. The method of claim 1 wherein the mammal is a human.

3. The method of claim 1 wherein the polymer is a poly(alkylene imine).

4. The method of claim 1 wherein the polymer is poly (decamethylenedimethylammonium-co-ethylenedimethylammonium) $X^-$, wherein $X^-$ is an anion, or poly(ethyleneimine).

5. The method of claim 1 wherein the gastrointestinal infection is an organism selected from the group consisting of Streptococcus, Salmonella, Campylobacter, *Escherichia coli, Clostridium difficile,* Staphyococcus, Shigella, Pneumocystis, *Cryptosporidium parvum, Giardia lamblia* and *Entamoeba histolytica.*

6. A method for treating a microbial infection in a mammal, comprising administering to the mammal a therapeutically effective amount of a polymer selected from the group consisting of poly(ethyleneimine) or poly (decamethylenedimethylammonium-co-ethyleneedimethylammonium) $X^-$, wherein $X^-$ is a pharmaceutically acceptable anion.

7. The method of claim 6 wherein the infection is an infection of the skin or an infection of the gastrointestinal tract.

8. The method of claim 6 wherein the microbial infection is a bacterial infection, a protozoal infection, an ameobic infection, a fungal infection or a parasitic infection.

9. The method of claim 8 wherein the infection is an infection by an organism selected from the group consisting of Streptococcus, Salmonella, Campylobacter, *Escherichia coli, Clostridium difficile,* Staphylococcus, Shigella, Pnuemocystis, *Cryptosporidium parvum, Giardia lamblia* and *Entamoeba histolytica.*

* * * * *

UNITED STATES PATENT AND TRADEMARK OFFICE
CERTIFICATE OF CORRECTION

PATENT NO. : 6,034,129
DATED : March 7, 2000
INVENTOR(S) : W. Harry Mandeville, III, Thomas X. Neenan, Stephen Randall Holmes-Farley It is certified that error appears in the above-identified patent and that said Letters Patent is hereby corrected as shown below:

Column 20, line 10, after "an" insert --- infection by an ---;
Column 20, line 12, "Staphyococcus" to --Staphylococcus--.
Column 20, line 20, "co-ethyleneedimethylammonium" should be
    --- co-ethylenedimethylammonium---.

Signed and Sealed this

Thirtieth Day of January, 2001

*Attest:*

Q. TODD DICKINSON

*Attesting Officer*  Director of Patents and Trademarks